(12) United States Patent
Tenenbaum et al.

(10) Patent No.: US 9,949,810 B2
(45) Date of Patent: Apr. 24, 2018

(54) SAFE METHOD FOR BLEACHING TEETH

(71) Applicant: COLGATE-PALMOLIVE COMPANY, New York, NY (US)

(72) Inventors: Fabian Tenenbaum, Tenafly, NJ (US); Lion Flyash, Nazareth-Illit (IL)

(73) Assignee: Colgate-Palmolive Company, New York, NY (US)

( * ) Notice: Subject to any disclaimer, the term of this patent is extended or adjusted under 35 U.S.C. 154(b) by 171 days.

(21) Appl. No.: 14/449,186

(22) Filed: Aug. 1, 2014

(65) Prior Publication Data

US 2016/0030145 A1 Feb. 4, 2016

(51) Int. Cl.
*A61C 19/06* (2006.01)
*A61K 8/22* (2006.01)
*A61Q 11/00* (2006.01)

(52) U.S. Cl.
CPC .............. *A61C 19/066* (2013.01); *A61K 8/22* (2013.01); *A61Q 11/00* (2013.01); *A61K 2800/83* (2013.01); *A61K 2800/884* (2013.01)

(58) Field of Classification Search
CPC ......... A61C 19/066; A61K 8/22; A61Q 11/00
USPC ..................... 433/215, 80, 32; 424/53, 49
See application file for complete search history.

(56) References Cited

U.S. PATENT DOCUMENTS

| 7,775,795 | B2 | 8/2010 | Khawaled et al. | |
| 8,377,423 | B2 | 2/2013 | Speronello et al. | |
| 8,660,669 | B2 * | 2/2014 | Nemeh | A61C 19/063 433/216 |
| 2007/0122769 | A1 | 5/2007 | Levine | |
| 2012/0315596 | A1 * | 12/2012 | Gan | A61C 19/066 433/32 |
| 2013/0072851 | A1 * | 3/2013 | Doll | A61N 1/32 604/20 |

OTHER PUBLICATIONS

Dahl, et al., 2003, "Tooth bleaching—A critical review of the biological aspects," Critical Reviews in Oral Biology Medicine 14(4):292-304.
International Search Report and Written Opinion in International Application No. PCT/IL2015/050748, dated Dec. 18, 2015.

* cited by examiner

*Primary Examiner* — Pedro Philogene
*Assistant Examiner* — David C Comstock

(57) ABSTRACT

A safe method for bleaching teeth applies a thin film of a first bleaching composition having a high concentration of a bleaching agent to teeth to be bleached immediately followed by applying a second bleaching composition having a low concentration of a bleaching agent to teeth to be bleached.

18 Claims, 1 Drawing Sheet

SAFE METHOD FOR BLEACHING TEETH

TECHNOLOGY FIELD

The present method relates to the field of dental whitening and in particular to methods of use of dental bleaching compositions.

BACKGROUND

Stained or discolored teeth are considered as a cosmetic impairment. Teeth's whitening is a cosmetic treatment done to improve the appearance of teeth. Teeth are whitened to remove impairments such as those resulting from the effects of coffee, cigarettes, and other substances that permanently stain or discolor teeth. Different techniques of teeth whitening or bleaching are known and relatively simple procedures improving the stained teeth appearance exist. The procedures can be conducted in a dental clinic, office or in a residential environment.

A variety of dental bleaching compositions and dental bleaching devices or trays exist on the market. Such dental bleaching compositions are typically applied to a person's teeth using a dental tray configured so as to retain the dental composition against the person's teeth. Treatment time can vary between about 10 minutes to a few hours and although conducted in a residential environment it can temporarily limit the user's freedom of speech, movement and function during the treatment period. In addition, it is uncomfortable for the user to keep a dental tray in the mouth over relatively long periods of time. User comfort during the teeth bleaching treatment duration may be improved by shortening the time of bleaching.

Most common bleaching agents used are peroxides, including but not limited to hydrogen peroxide, carbamide peroxide, sodium perborate, and sodium percarbonate. The simplest way to shorten the treatment time can be to increase the concentration of the peroxide. However, use of higher concentrations of bleaching agents (e.g., peroxides) can result in irritation and even some damage of oral mucosa such as gums or lips or other soft tissue.

As a result, the current methods of application of bleaching agents disclose using lower concentrations of bleaching agents, applying protection to the gums such as a protective light curable gingival protector or similar prior to application of the bleaching agent or using bleaching agents other than hydrogen peroxide such as chlorine dioxide and oxychlorine anions (U.S. Pat. No. 8,377,423).

Another way to accelerate bleaching time and speed up the chemical reaction related to the bleaching process can be concurrent application of heat or light or DC (Direct Current) electric current to the bleaching composition as disclosed in U.S. Pat. No. 7,775,795.

SUMMARY

Presented is a method of safe application of a dental bleaching agent, mainly hydrogen peroxide to teeth to speed up and shorten a teeth whitening treatment session while maintaining the safety of the treatment. The method can include applying initially a first dental whitening composition having a high concentration of a bleaching agent (e.g., hydrogen peroxide) to the teeth followed by applying a second dental whitening composition having a low concentration of a bleaching agent.

The method can also include generating DC electrical current through the mixture of the applied dental whitening compositions so that to accelerate the activity of the bleaching agent and further shorten the teeth whitening treatment time.

The first dental whitening composition having a high concentration of the bleaching agent and the second dental whitening composition having a low concentration of a bleaching agent can be applied consecutively and/or concurrently during the same teeth whitening treatment session.

The method also includes applying the first dental whitening composition having a high concentration of the bleaching agent and the second dental whitening composition having a low concentration of a bleaching agent together and allowing sufficient time so that the bleaching agent concentration within the mixture of the compositions stabilizes by diffusion at a concentration sufficiently high to whiten the teeth but not cause any irritation to the oral mucosa.

The first composition is operative to penetrate deep within the enamel wherein the high concentration of the hydrogen peroxide in the first composition operates to erase most of embedded stains. Applying the second composition to the same stains for a same period of time would not affect the embedded stains affected by the first composition. Hence, the first composition penetrates deep within the enamel to erase most of embedded stains not affectable by the second composition when applied for a same period of time.

The bleaching agent (e.g., hydrogen peroxide) can be an ingredient in, for example, a whitening gel being, for example, a composition of one or more ingredients including hydrogen peroxide as a bleaching agent, a cross-linked polyacrylate polymer as a thickening component, and the electrical conductivity enhancing ingredients such as electrolytes. Potassium nitrate and/or potassium hydroxide are examples of such electrolytes. Each of them could be included alone in the composition or a mix of both of them could be used to enhance conductivity of the dental bleaching gel composition.

Other ingredients can include Glycerin, propylene glycol and water are used as vehicles and solvents in which other ingredients or components are mixed to prepare the dental bleaching gel composition.

Other ingredients affecting antimicrobial and oxidizing properties of the gel, mouth refreshing components and components improving bleaching gel viscosity and wetting properties are added as required to the composition.

The concentration of bleaching agent in the composition can vary (i.e., lower) over time so that to drop below a concentration level that can irritate the oral mucosa.

Applying the dental whitening composition or gel could be done by placing the composition or gel in a dental cosmetic treatment tray or applicator configured to retain the dental composition against the person's dental arcade, such as the Pearl® applicator commercially available from Iluminage Beauty LTD, Yokneam Industrial Zone, 2069201 ISRAEL).

DESCRIPTION

Figure 1:
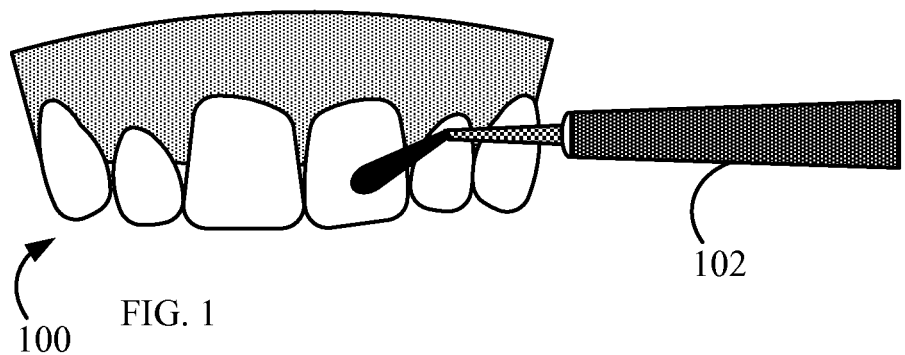
FIG. 1 is a frontal view simplified illustration of an example of a first step of a safe method for cosmetic whitening of teeth.

In the context of the present disclosure the terms "dental bleaching" and "dental whitening" have the same meaning.

DC electric current is known to accelerate the bleaching reaction. The DC electric current activates the bleaching agent and accelerates the bleaching reaction. The DC current activates certain ingredients of a specially formulated whitening gel, allowing it to penetrate deep within the enamel to erase most of embedded stains without sensitivity or irritation. Use of DC electrical current and specially formulated gel has proved to deliver whitening results much better than light or heat activated teeth whitening treatments.

The term "dental whitening composition having a high concentration of hydrogen peroxide" and "the first composition" mean the same and refer to a dental whitening bleaching agent composition having a concentration of hydrogen peroxide between 20% and 50% (w/v).

The term "dental whitening composition having a low concentration of hydrogen peroxide" and "the second composition" mean the same and refer to a dental whitening bleaching agent composition having a concentration of hydrogen peroxide between 0.1%-15% (w/v).

As described above, applying bleaching agents such as hydrogen peroxide to teeth could be harmful to the oral mucosa and other adjacent soft tissue. However the effect of a bleaching agent such as hydrogen peroxide on tissue depends not only on the concentration of the bleaching agent in the applied bleaching composition but also on the length of contact time (i.e., direct contact) of the bleaching agent with the tissue.

Application of higher concentrations of hydrogen peroxide, e.g., concentrations between 20% and 50% (w/v) can be highly effective whitening or bleaching teeth however, contact time must be short in order to avoid irritation to oral mucosa and other soft tissue.

On the other hand, a low concentration of hydrogen peroxide, e.g., concentrations of 0.1%-15% (w/v) can be safer to oral mucosa and other adjacent soft tissue but can require and extended contact time to be effective and whiten teeth satisfactorily. Another aspect of treatment with hydrogen peroxide is that the longer the contact time of hydrogen peroxide, even at lower concentrations, the higher the risk of afflicting irritation to the oral mucosa and adjacent soft tissue.

The below described method combines a first dental whitening composition having a high concentration (20% and 50% (w/v)) and a second dental whitening composition having a low concentration (0.1%-15% (w/v)) of a bleaching agent applied for a longer duration and allowing sufficient application time of the mixture so that over time the bleaching agent concentration within the mixture of the compositions in contact with the teeth and oral mucosa stabilizes by diffusion at a concentration sufficiently high to whiten the teeth but not cause any irritation to the oral mucosa and adjacent soft tissue. In other words, the concentration of the bleaching agent in the whitening composition in contact with the teeth and oral mucosa is different and can vary (i.e., become lower) over time by diffusion so that to drop below a concentration that can irritate the oral mucosa.

The first dental whitening composition is operative to penetrate deep within the enamel wherein the high concentration of the hydrogen peroxide in the first dental whitening composition operates to erase most of embedded stains. Applying the second dental whitening composition to the same stains for a same period of time would not affect the embedded stains affected by the first dental whitening composition. Hence, the first composition penetrates deep within the enamel to erase most of embedded stains not affectable by the second composition when applied for a same period of time.

Figure 2:
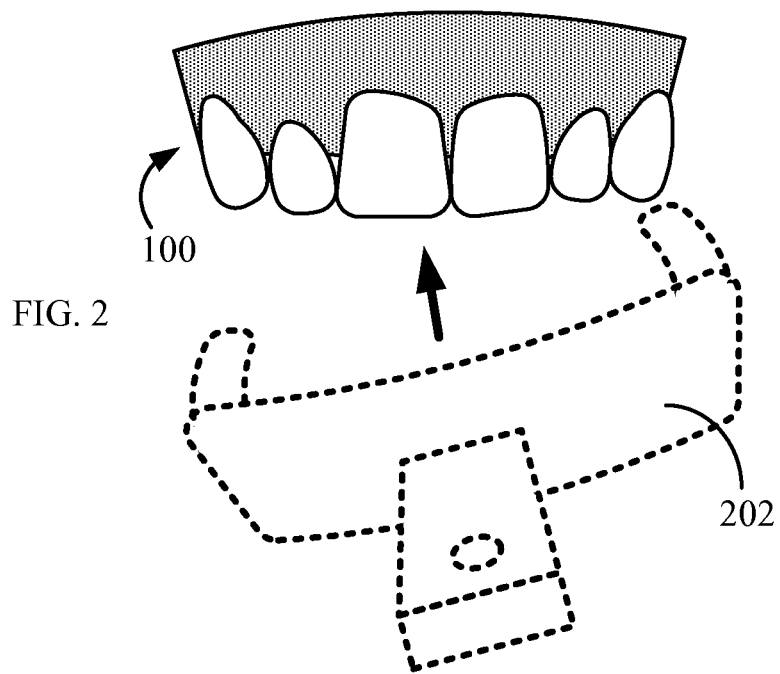
FIG. 2 a frontal view simplified illustration of a second step of an example of a safe method for cosmetic whitening of teeth.

Applying the first dental whitening composition or gel could be done by means of an applicator or brush 102 (FIG. 1). Applying the second dental whitening composition or gel to the teeth can be done by placing the second dental whitening composition in a cosmetic treatment tray or applicator 202 (FIG. 2) configured so as to retain the dental composition against the person's dental arcade 100 (FIG. 1). The tray or applicator could be such as the Pearl® applicator commercially available from Iluminage Beauty LTD, Yokneam Industrial Zone, ISRAEL and depicted in FIG. 2 by phantom lines.

The method includes applying a thin film of a first composition (FIG. 1) having a high concentration of a bleaching agent for a very short duration immediately followed by applying a second composition (FIG. 2) including a low, safe concentration of a bleaching agent without irritation of the oral mucosa and other adjacent soft tissue and allowing sufficient time so that the bleaching agent concentration within the mixture of the compositions stabilizes by diffusion at a concentration sufficiently high to whiten the teeth but not cause any irritation to the oral mucosa.

Figure 3:
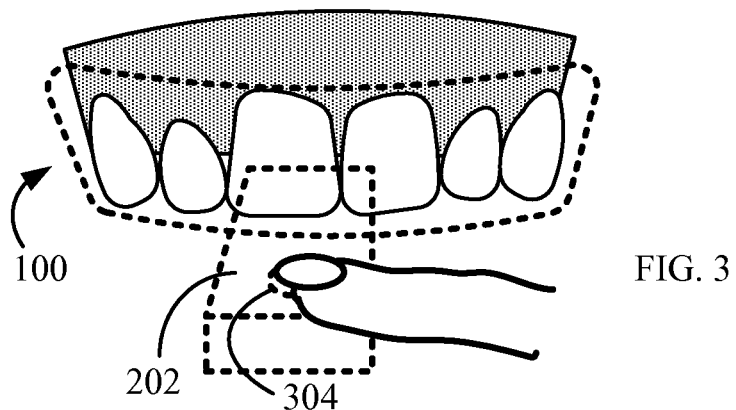
FIG. 3 a frontal view simplified illustration of yet another step of an example of a safe method for cosmetic whitening of teeth.

Additionally and optionally, the bleaching gel could also include one or more electrical conductivity enhancing ingredients such as electrolytes. When using a bleaching gel including electrical conductivity enhancing ingredients, the method of application could include applying a thin film of a first dental bleaching gel (FIG. 1) producing a high concentration of hydrogen peroxide (i.e., 20% and 50%) immediately followed by applying to the treated teeth an applicator 202 (FIG. 2) including a second dental bleaching gel (not shown) producing a low concentration of hydrogen peroxide (i.e., 0.1% and 15%) and activating applicator 202 by pressing on an ON/OFF button 304 (FIG. 3) and applying a DC current through the mixture of compositions retained in the applicator and in contact with the teeth so that to accelerate the bleaching activity of the hydrogen peroxide on teeth and shorten the teeth bleaching treatment time.

The first dental whitening composition having a high concentration of the bleaching agent and the second dental whitening composition having a low concentration of a bleaching agent can be applied consecutively and/or concurrently during the same teeth whitening treatment session.

The bleaching agent can be an ingredient in, for example, a whitening gel being, for example, a composition of one or more ingredients including hydrogen peroxide as a bleaching agent, a cross-linked polyacrylate polymer as a thickening component, and the electrical conductivity enhancing ingredients such as electrolytes. Potassium nitrate and/or potassium hydroxide are examples of such electrolytes. Each of them could be included alone in the composition or a mix of both of them could be used to enhance conductivity of the dental bleaching gel composition.

Other ingredients can include Glycerin, propylene glycol and water are used as vehicles and solvents in which other ingredients or components are mixed to prepare the dental bleaching gel composition.

Other ingredients affecting antimicrobial and oxidizing properties of the gel, mouth refreshing components and components improving bleaching gel viscosity and wetting properties are added as required to the composition.

It will be appreciated by persons skilled in the art that the present methods are not limited to what has been particularly shown and described hereinabove. Rather, the scope of the methods includes both combinations and sub-combinations of various features described hereinabove as well as modifications and variations thereof which would occur to a person skilled in the art upon reading the foregoing description and which are not in the prior art.

What is claimed is:

1. A method for bleaching teeth comprising:
    applying a first bleaching composition having a first concentration of a first bleaching agent to teeth to be bleached;
    subsequently applying a second bleaching composition having a second concentration of a second bleaching agent to the teeth while the first bleaching composition remains on the teeth; and
    wherein the second concentration of the second bleaching agent in the second bleaching composition is less than the first concentration of the first bleaching agent in the first bleaching composition.

2. The method according to claim 1, wherein the first bleaching agent in the first bleaching composition is hydrogen peroxide at a concentration between 20% and 50% (w/v).

3. The method according to claim 1, wherein the second bleaching agent in the second bleaching composition is hydrogen peroxide at a concentration of between 0.1% and 15% (w/v).

4. The method according to claim 1, wherein the second bleaching composition is applied to the teeth immediately following the application of the first bleaching composition to the teeth during the same teeth whitening treatment session so that the first and second bleaching compositions mix together to form a mixed bleaching composition having a mixed bleaching agent.

5. The method according to claim 4, wherein the mixed bleaching agent is a mixture of the first and second bleaching agents, and wherein the mixed bleaching composition comprises a third concentration of the mixed bleaching agent, the third concentration of the mixed bleaching agent in the mixed bleaching composition being less than the first concentration of the first bleaching agent in the first bleaching composition.

6. The method according to claim 5, further comprising leaving the mixed bleaching composition on the teeth for a sufficient period of time so that the third concentration of the mixed bleaching agent in the mixed bleaching composition stabilizes by diffusion, the third concentration of the mixed bleaching agent in the mixed bleaching composition decreasing over time until stabilizing.

7. The method according to claim 1, wherein the first and second bleaching agents are the same and are one of hydrogen peroxide, carbamide peroxide, sodium perborate, and sodium percarbonate.

8. The method according to claim 7, wherein the first and second bleaching agents are hydrogen peroxide.

9. The method according to claim 1, wherein the first bleaching agent in the first bleaching composition has a concentration between 20% and 50% (w/v) and the second bleaching agent in the second bleaching composition has a concentration between 0.1% and 15% (w/v).

10. A method for bleaching teeth comprising:
    applying a first bleaching composition having a first concentration of a first bleaching agent to teeth to be bleached;
    subsequently, while the first bleaching composition remains on the teeth, applying a second bleaching composition having a second concentration of a second bleaching agent to the teeth, wherein the second concentration of the second bleaching agent in the second bleaching composition is less than the first concentration of the first bleaching agent in the first bleaching composition; and
    the first and second bleaching compositions mixing together on the teeth to form a mixed bleaching composition having a mixed bleaching agent that is a mixture of the first and second bleaching agents, wherein the mixed bleaching composition comprises a third concentration of the mixed bleaching agent, the third concentration of the mixed bleaching agent in the mixed bleaching composition being less than the first concentration of the first bleaching agent in the first bleaching composition.

11. The method according to claim 10, wherein the first bleaching agent in the first bleaching composition is hydrogen peroxide at a concentration between 20% and 50% (w/v).

12. The method according to claim 11, wherein the second bleaching agent in the second bleaching composition is hydrogen peroxide at a concentration of between 0.1% and 15% (w/v).

13. The method according to claim 10 further comprising applying a DC current through the mixed bleaching composition, the mixed bleaching composition retained in an applicator and in contact with the teeth.

14. The method according to claim 10 wherein the third concentration of the mixed bleaching agent in the third bleaching composition decreases over time due to diffusion.

15. A method for shortening bleaching teeth treatment time comprising:
    applying a first bleaching composition having a first concentration of a first bleaching agent to teeth to be bleached;
    subsequently applying a second bleaching composition having a second concentration of a second bleaching agent to the teeth; and
    wherein the first bleaching agent in the first bleaching composition is hydrogen peroxide at a concentration between 20% and 50% (w/v), the first bleaching composition penetrating deep within the enamel to erase embedded stains.

16. The method according to claim 15, wherein the second bleaching composition is disposed within an applicator that is applied to the teeth, and further comprising activating the applicator to apply a DC current through the first and second bleaching compositions while the first and second bleaching compositions are retained in the applicator and in contact with the teeth.

17. The method according to claim 15, wherein the second bleaching agent in the second bleaching composition is hydrogen peroxide at a concentration of between 0.1% and 15% (w/v).

18. The method according to claim 15 wherein the first and second bleaching agents are hydrogen peroxide.

* * * * *